(12) United States Patent
Smyth et al.

(10) Patent No.: US 10,272,158 B2
(45) Date of Patent: Apr. 30, 2019

(54) COMPOUNDS FOR TREATING BIOFILM INFECTION

(71) Applicant: Board of Regents, The University of Texas System, Austin, TX (US)

(72) Inventors: Hugh Smyth, Austin, TX (US); Ju Du, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/323,482

(22) PCT Filed: Jul. 2, 2015

(86) PCT No.: PCT/US2015/039009
§ 371 (c)(1),
(2) Date: Jan. 3, 2017

(87) PCT Pub. No.: WO2016/004321
PCT Pub. Date: Jan. 7, 2016

(65) Prior Publication Data
US 2017/0143842 A1    May 25, 2017

Related U.S. Application Data

(60) Provisional application No. 62/020,775, filed on Jul. 3, 2014.

(51) Int. Cl.
*A61K 47/60* (2017.01)
*A61K 31/7036* (2006.01)
*A61K 45/06* (2006.01)

(52) U.S. Cl.
CPC .......... *A61K 47/60* (2017.08); *A61K 31/7036* (2013.01); *A61K 45/06* (2013.01); *Y02A 50/473* (2018.01); *Y02A 50/475* (2018.01); *Y02A 50/478* (2018.01); *Y02A 50/481* (2018.01)

(58) Field of Classification Search
CPC ..... A61K 47/60; A61K 31/7036; A61K 45/06
See application file for complete search history.

(56) References Cited

U.S. PATENT DOCUMENTS

| | | | |
|---|---|---|---|
| 7,585,837 B2 * | 9/2009 | Shechter | A61K 47/48215 514/1.1 |
| 2005/0008671 A1 | 1/2005 | Van Antwerp | |
| 2010/0286031 A1 * | 11/2010 | Charan | A61K 9/0078 514/3.1 |
| 2013/0171224 A1 | 7/2013 | Percival et al. | |
| 2014/0256660 A1 | 9/2014 | Sinha et al. | |

OTHER PUBLICATIONS

Zalipsky, S., Adv. Drug Delivery Rev., (1995), 16, p. 157-182. (Year: 1995).*
Du et al., Mol. Pharmaceutics, 2015, 12, p. 1544-1553, published Mar. 20, 2015. (Year: 2015).*
Aaron, S.D., Antibiotic synergy testing should not be routine for patients with cystic fibrosis who are infected with multiresistant bacterial organisms. Paediatr Respir Rev, 8(3): p. 256-61, 2007.
Alconcel el al., "FDA-approved poly (ethylene glycol)—protein conjugate drugs." Polymer Chemistry 2.7 (2011): 1442-1448.
Costerton el al., "Bacterial biofilms: a common cause of persistent infections." Science 284.5418 (1999): 1318-1322.
De Hoog et al., New dosing strategies for antibacterial agents in the neonate. Semin Fetal Neonatal Med, 10(2): p. 185-94, 2005.
Dodge et al., Cystic fibrosis mortality and survival in the UK: 1947-2003. Eur Respir J, 29(3): p. 522-6, 2007.
Flemming and Wingender, The biofilm matrix. Nature Reviews Microbiology, 8(9): p. 623-633, 2010.
Fux et al., Survival strategies of infectious biofilms Trends Microbiol, 13(1): p. 34-40, 2005.
George et al., Cystic fibrosis infections: treatment strategies and prospects. FEMS Microbiol Lett, 300(2): p. 153-64, 2009.
Gilligan, P.H., Microbiology of airway disease in patients with cystic fibrosis. Clin Microbiol Rev, 4(1): p. 35-51, 1991.
Hancock et al., Interaction of aminoglycosides with the outer membranes and purified lipopolysaccharide and OmpF porin of *Escherichia coli*. Antimicrobial agents and chemotherapy, 35(7): p. 1309-1314, 1991.
Høiby, N., Recent advances in the treatment of Pseudomonas aeruginosa infections in cystic fibrosis. BMC medicine, 9(1): p. 32, 2011.
International Preliminary Report on Patentability issued in International Application No. PCT/US2015/039009, dated Jan. 12, 2017.
International Search Report and Written Opinion issued in International Application No. PCT/US2015/039009, dated Dec. 7, 2015.
Invitation to Pay Additional Fees issued in International Application No. PCT/US2015/039009, dated Sep. 8, 2015.
Jana and Deb, Molecular understanding of aminoglycoside action and resistance. Applied microbiology and biotechnology, 70(2): p. 140-150, 2006.
Kotra et al., Aminoglycosides: perspectives on mechanisms of action and resistance and strategies to counter resistance. Antimicrobial agents and chemotherapy, 44(12): p. 3249-3256, 2000.

(Continued)

*Primary Examiner* — Jonathan S Lau
(74) *Attorney, Agent, or Firm* — Parker Highlander PLLC

(57) ABSTRACT

In some aspects, pegylated aminoglycoside compounds are provided. In some embodiments, m-PEG-tobramycin compounds may be used to treat a biofilm infection or reduce or treat established biofilms. The present invention provides, in various aspects, compounds and methods for the treatment of infections, such as biofilm infections or chronic biofilm infections. The chronic biofilm infection may occur in wounds, implanted devices, immunocompromised patients, people with cystic fibrosis, eye infections, etc.

20 Claims, 9 Drawing Sheets

(56) References Cited

OTHER PUBLICATIONS

Luten et al., Degradable PEG-folate coated poly(DMAEA-co-BA)phosphazene-based polyplexes exhibit receptor-specific gene expression. Eur J Pharm Sci, 33(3): p. 241-51, 2008.

MacLeod et al., Annnoglycoside-resistance mechanisms for cystic fibrosis Pseudomonas aeruginosa isolates are unchanged by long-term, intermittent, inhaled tobramycin treatment. Journal of Infectious Diseases, 181(3): p. 1180-1184, 2000.

Marcus et al., "Turning low-molecular-weight drugs into prolonged acting prodrugs by reversible pegylation: a study with gentamicin." *Journal of medicinal chemistry* 51.14 (2008): 4300-4305.

Mesaros et al., Pseudomonas aeruginosa: resistance and therapeutic options at the turn of the new millennium. Clin Microbiol Infect, 13(6): p. 560-78, 2007.

Pier, G.B., The challenges and promises of new therapies for cystic fibrosis. J Exp Med,. 209(7): p. 1235-9, 2012.

Popielarski et al., A nanoparticle-based model delivery system to guide the rational design of gene delivery to the liver. 1. Synthesis and characterization. Bioconjug Chem, 16(5): p. 1063-70, 2005.

Ramsey and Wozniak, Understanding the control of Pseudomonas aeruginosa alginate synthesis and the prospects for management of chronic infections in cystic fibrosis. Molecular microbiology, 56(2): p. 309-322, 2005.

Ramsey et al., Intermittent administration of inhaled tobramycin in patients with cystic fibrosis. Cystic Fibrosis Inhaled Tobramycin Study Group. N Engl J Med, 340(1): p. 23-30, 1999.

Ratjen and Doring, Cystic fibrosis. Lancet, 361(9358): p. 681-9, 2003.

Ratjen, F.A., Cystic fibrosis: pathogenesis and future treatment strategies. Respir Care, 54(5): p. 595-605, 2009.

Shaul et al., "Assessment of 6'-and 6'''-N-acylation of aminoglycosides as a strategy to overcome bacterial resistance," *Organic & biomolecular chemistry* 9.11 (2011): 4057-4063.

Stewart, "Theoretical aspects of antibiotic diffusion into microbial biofilms."*Antimicrobial agents and chemotherapy* 40.11 (1996): 2517-2522.

Strateva and Yordanov, Pseudomonas aeruginosa—a phenomenon of bacterial resistance. J Med Microbiol, 58(Pt 9): p. 1133-48, 2009.

Tre-Hardy et al., Evaluation of long-term co-administration of tobramycin and clarithromycin in a mature biofilm model of cystic fibrosis clinical isolates of Pseudomonas aeruginosa. Int J Antimicrob Agents, 34(4): p. 370-4. 2009.

Veronese et al., "PEG—doxorubicin conjugates: influence of polymer structure on drug release, in vitro cytotoxicity, biodistribution, and antitumor activity." *Bioconjugate chemistry*16.4 (2005): 775-784.

Wagner and Iglewski, P. aeruginosa biofilms in CF infection. Clinical reviews in allergy & immunology, 35(3): p. 124-134, 2008.

Woodward et al., Budget impact model of tobramycin inhalation solution for treatment of Pseudomonas aeruginosa in cystic fibrosis patients. J Med Econ, 13(3): p. 492-9, 2010.

Wu, et al., A new biodegradable polymer: PEGylated chitosan-g-PEI possessing a hydroxyl group at the PEG end. Journal of Polymer Research, 15(3): p. 181-185, 2008.

Yang and Lemma, "Penicillin V-conjugated PEG-PAMAM star polymers." *Journal of Biomaterials Science, Polymer Edition* 14.10 (2003): 1043-1056.

Zhang and Mah, Involvement of a novel efflux system in biofilm-specific resistance to antibiotics. Journal of bacteriology, 190(13): p. 4447-4452, 2008.

\* cited by examiner

H-NMR spectrum of tobramycin, PEG 5K, and PEG-Tobramycin (Tob-PEG) in D$_2$O.
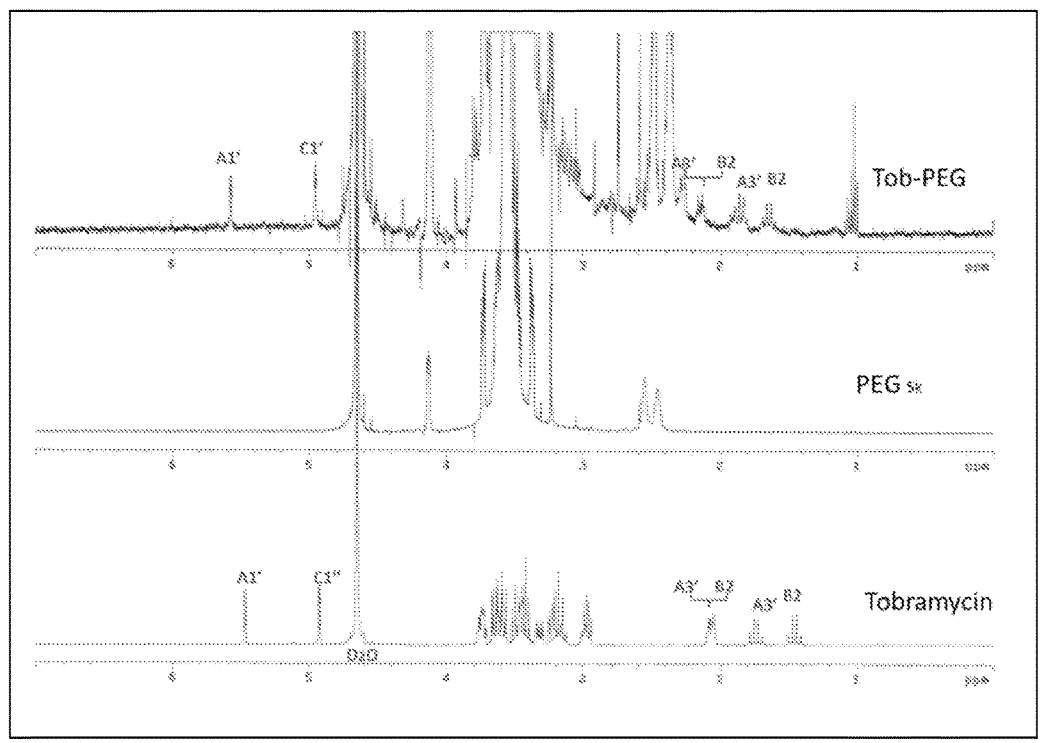
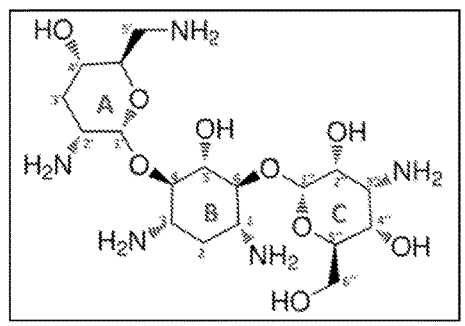
FIG. 1

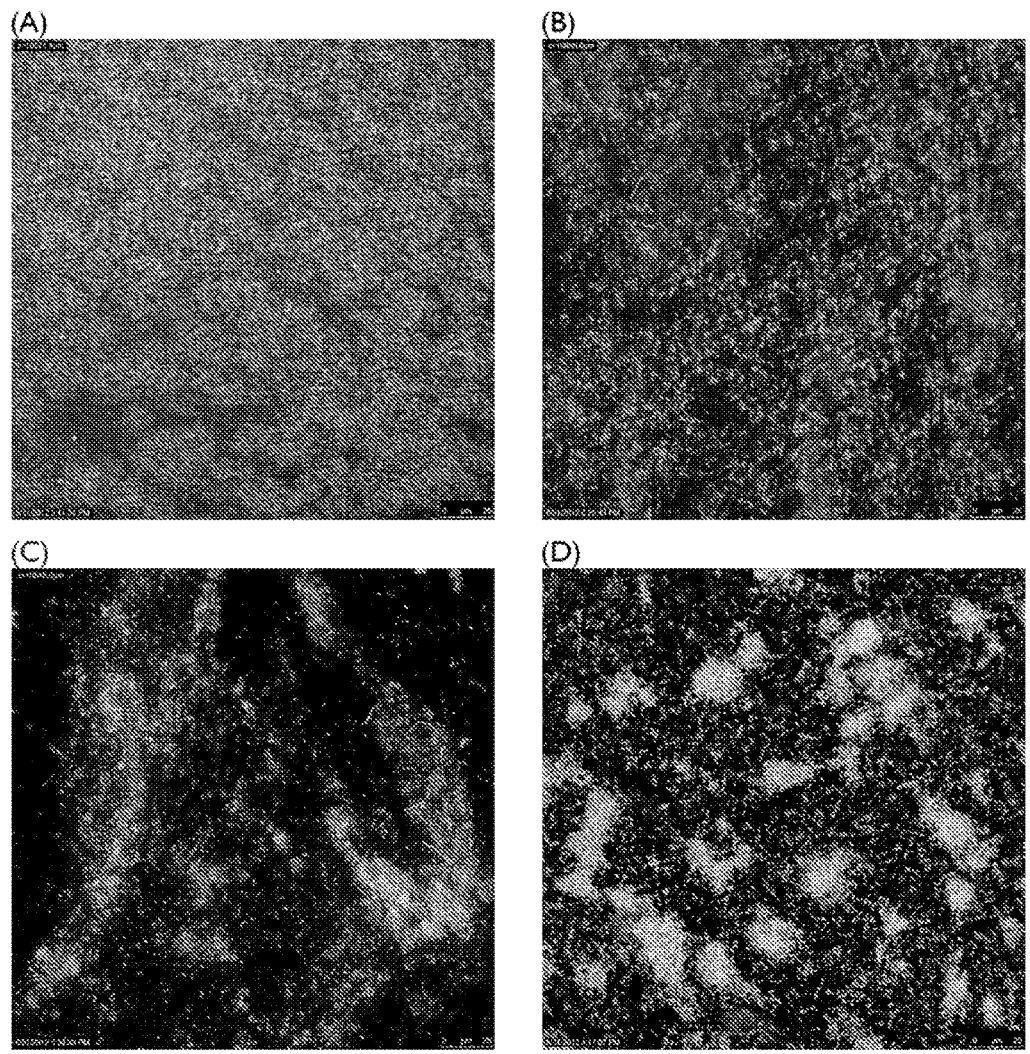
FIGS. 6A-D

COMPOUNDS FOR TREATING BIOFILM INFECTION

This application is a national phase application under 35 U.S.C. § 371 of International Application No. PCT/US2015/039009, filed Jul. 2, 2015, which claims the benefit of U.S. Provisional Patent Application No. 62/020,775, filed Jul. 3, 2014, the entirety of which are incorporated herein by reference.

BACKGROUND OF THE INVENTION

1. Field of the Invention

The present invention relates generally to the field of pharmacology and medicine. More particularly, it concerns hydrophilic polymer conjugated antibacterial agents, such as pegylated aminoglycosides for the treatment of infections such as, e.g., biofilm infections.

2. Description of Related Art

Biofilms are protective coats produced by bacterial communities that can allow bacteria to become resistant to treatment and can present very problematic and sometimes life-threatening chronic infections. The clinical treatment of biofilm infections often proves to be particularly problematic because they are difficult to treat and generally display a reduced sensitivity to regular antibiotics, e.g., resulting from protection from and encasement in the biofilm matrix.

Biofilm infections, such as pneumonia in cystic fibrosis patients, chronic wounds, chronic otitis media and implant- and catheter-associated infections, affect millions of people in the developed world each year and many deaths occur as a consequence. One of the important hallmarks of chronic biofilm-based infections is extreme resistance to antibiotics and many other conventional antimicrobial agents.

An example of a disease commonly associated with biofilm infections is cystic fibrosis. Cystic fibrosis (CF) is an inherited autosomal recessive disease that is commonly diagnosed at early childhood and can result in chronic infections (Ratjen and Doring, 2003). Prevalence varies among different ethnic populations (Dodge et al., 2007) and affects about 30,000 children and adults in the United States (70,000 worldwide) according to the Cystic Fibrosis Foundation. A defective cystic fibrosis transmembrane regulator (CFTR) causes faulty transport of sodium chloride in many parts of the body, including the lungs, intestine, pancreas and liver (Dodge et al., 2007), leading to thick and viscous mucus secretion. Over 1500 mutations in the chromosome 7 which codes for CFTR have been identified indicating the diversity of the disease and can present difficulties in management (Ratjen, 2009). As a result of thick and viscous mucous secretions, patients with CF are prone to repeated infections of *Pseudomonas aeruginosa*, *Staphylococcus aureus*, and *Haemophilus influenzae* (Dodge et al., 2007; Gilligan, 1991).

*P. aeruginosa* starts colonizing in the airway as a non-mucoid strain. As the infection progresses, the bacterium switch to a mucoid form and secrete excessive amount of extracellular matrix forming biofilm ultimately (George et al., 2009; Wagner and Iglewski, 2008; Ramsey and Wozniak, 2005). Biofilm, a self-produced matrix, consists of polysaccharides, proteins, and DNA (Flemming and Wingender, 2010). The formation of biofilm imposes a higher antibiotic resistance to *P. aeruginosa* in CF patients which can be up to 1000 times of the planktonic phase of *P. aeruginosa* (Aaron, 2007; Fux et al., 2005). The factors from biofilm that contributes antibiotic resistance includes: slow growth rates, low antibiotic penetration, internal hypoxic environment within the microcolonies, high cell density (up to 109 CFU/mL), excessive extracellular matrices, pH alterations, altered nutrient requirements (Ramsey et al., 1999). Hence the development of better treatments for biofilm related infections is a major focus in CF therapeutics investigations (Pier, 2012; Høiby, 2011).

Recently, FDA approved tobramycin inhalation powder for use in CF patients with *P. aeruginosa*. Despite clinical benefits of inhaled tobramycin, biofilm infections remain resistant against this drug (Strateva and Yordanov, 2009; Zhang and Mah, 2008; MacLeod et al., 2000). There is an urgent need to improve the efficacy of antibiotics. Antimicrobial agents are currently used as first line agents in infections yet typically have poor activity against the chronic biofilm infections. Clearly, there exists a need for improved compounds for treating biofilm infections.

SUMMARY OF THE INVENTION

The present invention provides, in various aspects, compounds and methods for the treatment of infections, such as biofilm infections or chronic biofilm infections. The chronic biofilm infection may occur in wounds, implanted devices, immunocompromised patients, people with cystic fibrosis, eye infections, etc. In some embodiments, compounds provided herein may be used to more effectively treat a biofilm infection or chronic biofilm infection than current therapeutic agents. In some aspects, pegylated aminoglycoside such as, e.g., pegylated tobramycin, are provided and may be used to treat an infection in a subject such as, e.g., a biofilm infection. As shown in the below examples, pegylated tobramycin has been observed to display an unexpected increase in treating biofilms such as pre-formed biofilms. In some embodiments, a pegylated aminoglycoside of the present invention may be administered in combination with a second antimicrobial compound to kill microorganisms in both biofilm and planktonic phase.

As shown in the below examples, the antimicrobial efficacy of an aminoglycoside to treat an established biofilm may be enhanced (e.g., ~3-5 times better efficacy) by pegylating the aminoglycoside (e.g., tobramycin), to create a new therapeutic entity. In some embodiments, these effects may be specific for treating biofilm infections or established biofilms. For example, for pegylated tobramycin significant improvements for the killing of established biofilms was observed, although killing of the same bacteria in a non-biofilm form (e.g., planktonic phase bacteria that are freely floating or non-adherent) was reduced as compared to non-pegylated tobramycin. Without wishing to be bound by any theory, the results support the idea that this modification can reduce or stop the antibiotic from being lost to binding sites on biofilm matrices. In some embodiments, a pegylated aminoglycoside may be administered to a subject in combination with a non-pegylated aminoglycoside to treat an infection in the subject.

As shown in the below examples, to overcome biofilm-associated antibacterial resistance, a new compound of Tobramycin-PEG (Tob-PEG) was developed via conjugating tobramycin to a polyethylene glycol (also referred to as poly(ethylene glycol) or PEG). Compared to tobramycin, Tob-PEG exhibited almost 10 fold inhibition concentration on *P. aeruginosa* in its planktonic phase and biofilm forming phase. However, Tob-PEG suppressed *P. aeruginosa* in its pre-formed biofilm phase with much lower concentration than tobramycin (27.81 μmol/L vs. 89.80 μmol/L). Physically mixed PEG and tobramycin (i.e., non-conjugated) behaved as same as tobramycin. In contrast, the Tob-PEG compound provided surprising and unexpected properties for overcoming bacterial resistance due to its biofilm formation.

In some embodiments, an aminoglycoside such as, e.g., tobramycin, is covalently attached to a poly(ethylene glycol). Nonetheless, in various aspects another water-soluble polymer may be substituted for the poly(ethylene glycol) such as, e.g., poly(alkylene glycol), poly(oxyethylated polyol), poly(olefinic alcohol), poly(vinylpyrolidone), poly(hydroxypropylmethacrylamide), poly(α-hydroxy acid), poly(vinyl alcohol), polyphosphazene, polyoxazoline, and copolymers and terpolymers thereof.

An aspect of the present invention relates to a compound comprising an aminoglycoside covalently bound to a poly(ethylene glycol). The aminoglycoside may be gentamicin, tobramycin, amikacin, streptomycin, neomycin, or paromomycin. In some embodiments, the aminoglycoside is tobramycin. The poly(ethylene glycol) may be linear or branched. The poly(ethylene glycol) may comprise the formula $CH_3-PEG-$. In some embodiments, the poly(ethylene glycol) comprises the formula $CH_3-[O-CH_2-CH_2]_n-$, wherein n=2-3000. The poly(ethylene glycol) may comprise the formula $CH_3-[O-CH_2-CH_2]_n-OC(O)CH_2CH_2C(O)-$, wherein n=2-3000. In some embodiments, n=100-2000. In some embodiments, wherein the compound has the structure

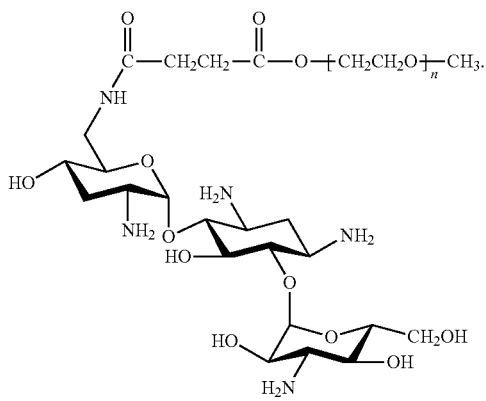

In some embodiments, n=2-3000. In some embodiments, n=100-2000. In some embodiments, the compound has a molecular weight ranging from about 100 daltons to about 100,000 daltons, from about 2000 daltons to about 20,000 daltons, or from about 2000 daltons to about 10,000 daltons. The compound may be comprised in a pharmaceutical composition. The pharmaceutical preparation may be formulated for topical, inhalational, parenteral, or intravenous administration. The pharmaceutical preparation may comprise a second antimicrobial, antibacterial, or antifungal compound such as, for example, an aminoglycoside (e.g., tobramycin).

Another aspect of the present invention relates to a method of treating a biofilm infection in a subject comprising administering to the subject a therapeutic amount of a pegylated aminoglycoside. The aminoglycoside portion of the pegylated aminoglycoside may be gentamicin, tobramycin, amikacin, streptomycin, neomycin, or paromomycin. In some embodiments, the aminoglycoside portion of the pegylated aminoglycoside is gentamicin, tobramycin, or amikacin. In some embodiments, the aminoglycoside portion of the pegylated aminoglycoside is tobramycin. The pegylated aminoglycoside may be further defined as a pegylated aminoglycoside as described above or herein. The pegylated portion of the pegylated aminoglycoside may comprise a PEG moiety having a molecular weight of 1500-7500 daltons. The subject may be a mammal. The mammal may be a human. The biofilm infection may comprise gram-negative bacteria such as, e.g., an anerobic bacteria or a facultative anaerobic bacteria. In some embodiments, the gram-negative bacteria is an aerobic gram negative bacteria. The biofilm infection may comprise gram-positive bacteria. In some embodiments, the biofilm infection comprises staphylococci such as, e.g., *Staphylococcus epidermidis, Staphylococcus aureus*, or MRSA. In some embodiments, the biofilm infection comprises *Pseudomonas aeruginosa, Staphylococcus aureus, Haemophilus influenza, Enterrococcus faecalis, Escherichia coli, Salmonella, Shigella*, an Enterobacteriaceae, *Pseudomonas, Moraxella, Helicobacter, Stenotrophomonas, Bdellovibrio*, a acetic acid bacteria, a fungal biofilm, *Legionella* or *Mycobacterium tuberculosis*. In some embodiments, the biofilm infection comprises *Pseudomonas aeruginosa*. The subject may have a second disease such as, e.g., cystic fibrosis, neutropenia, or HIV. The subject may be immunocompromised or have an immune dysfunction. In some embodiments, the subject has a burn or a wound infection. In some embodiments, the subject has pneumonia, septic shock, a urinary tract infection, a gastrointestinal infection, a skin infection, or a soft tissue infection. The biofilm infection may further comprise bacteria in a biofilm forming phase or a planktonic phase. The biofilm infection may comprise bacteria in a maturation II or dispersion biofilm phase. The biofilm infection may be on or in the skin of the subject. In some embodiments, the biofilm infection is on or adjacent to a medical device implanted in the subject. The medical device may be, e.g., a catheter, sutures, a staple, or a pin. In some embodiments, about 1-20 mg/kg/day or about 5-15 mg/kg/day of the pegylated aminoglycoside is administered to the subject. The method may further comprise administering a second antimicrobial, antibacterial, or antifungal compound to the subject. The second compound may be an aminoglycoside such as, e.g., tobramycin.

Yet another aspect of the present invention relates to a medical device, wherein at least a portion of a surface of the device is coated with a pegylated aminoglycoside of the present invention. In some embodiments, part of the surface is coated with the compound. In some embodiments, all or essentially all of the surface is coated with the compound. The medical device may be a glove, a catheter, a stent, a staple, a pin, an electrical nerve stimulation device, a screw, a rod, a wire, a collar, a tube, or a surgical drain. In some embodiments, the medical device is a catheter. The catheter may be an intravenous catheter, a drainage catheter, or a urinary catheter. The coating may further comprise a second antimicrobial, antibacterial, or antifungal compound. The second compound may be an aminoglycoside such as, e.g., tobramycin.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: H-NMR spectrum of Tobramycin, PEG 5K, and PEG-Tobramycin in $D_2O$.

FIGS. 6A-D: Confocal images of *P. aeruginosa* biofilms. Stained with Live/Dead BacLight Bacterial Viability kit. Live cells are stained in green and dead cells are in red (×63). (FIG. 6A) Control *P. aeruginosa* biofilm; note the dense colonization and spatial orientation. (FIG. 6B) Treated with PEG; note that the biofilm still possesses the complex structure and viability. (FIG. 6C) Treated with tobramycin; note that the biofilm architecture is seriously disturbed and higher proportions of dead cells compared to the control. (FIG. 6D) Treated with Tob-PEG; note the weak biofilm structure and lack of extracellular substances and dead cell count is higher than that in tobramycin treated sample.

(FIG. 7A) Control *P. aeruginosa* biofilm; biofilm was densely colonized and extracellular substances were also visible. (FIG. 7B) Treated with PEG, similar to control, biofilm was well organized with substantial amount of extra cellular matrix. (FIG. 7C) Treated with tobramycin; note the scanty biofilm architecture and the presence of extra cellular matrix. (FIG. 7D) Treated with Tob-PEG; note the isolated bacterial cells with no biofilm architecture and complete absence of extracellular matrix.

(FIG. 8A) alginate solution droplet; (FIG. 8B) interaction between alginate and tobramycin; (FIG. 8C) interaction between alginate and Tob-PEG; (FIG. 8D) interaction between alginate and the mixture of tobramycin and PEG; (FIG. 8E) interaction between alginate and PEG. Bar: 2.0 mm.

DESCRIPTION OF ILLUSTRATIVE EMBODIMENTS

Figure 2:
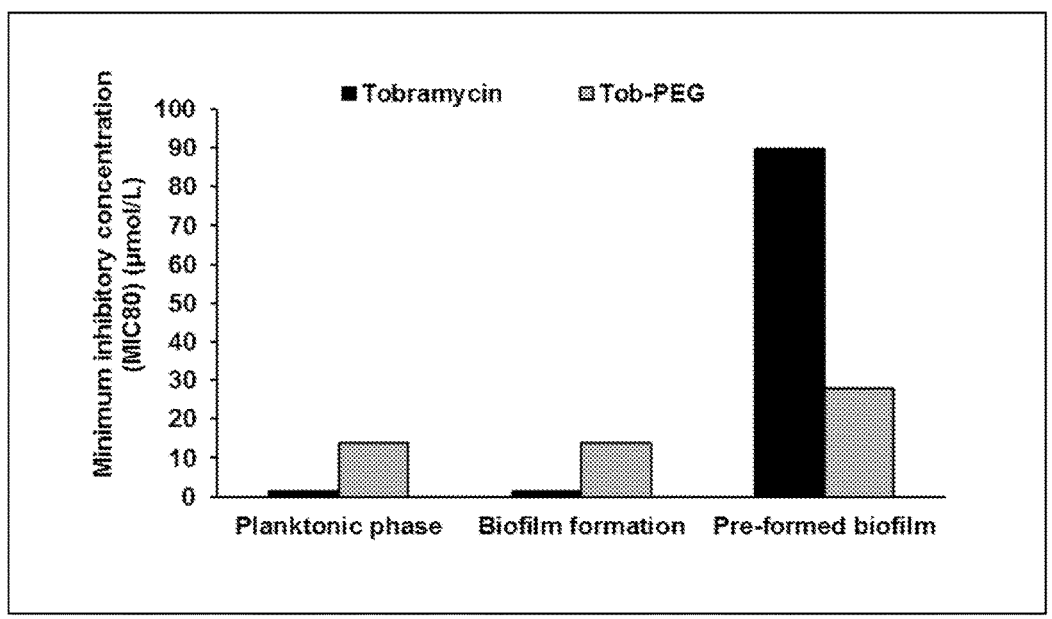
FIG. 2: Minimum inhibitory concentration (MIC80) of tobramycin, and Tob-PEG in planktonic phase, biofilm formation process and pre-formed biofilm (24 h) of *P. aeruginosa*. (MIC80±SD, SD=0, n=12, experiments were performed in quadruplicates at three times. The broth dilution assay resulted in the same value of the drug concentration for MIC80, thus SD is 0); note the significant low concentration of Tob-PEG needed to inhibit *P. aeruginosa* pre-formed biofilm compared to pure tobramycin.

In certain aspects, compounds that display enhanced antibiotic activity, e.g., for the treatment or killing of bacterial biofilms are provided. For example, pegylated aminoglycosides such as polyethylene glycol conjugated forms of tobramycin (Tob-PEG) are provided and can be synthesized (e.g., via site specific conjugation of polyethylene glycol to tobramycin).

As shown in the below examples, antibacterial activities of Tob-PEG were determined on *Pseudomonas aeruginosa* in planktonic phase, biofilm forming phase, pre-formed biofilm phase, and also in a time-dependent biofilm elimination model. In planktonic and biofilm formation phase of *P. aeruginosa*, Tob-PEG exhibited approximately 10 fold higher inhibition concentration than tobramycin, indicating lower antimicrobial activity. However, in pre-formed biofilm based *P. aeruginosa*, Tob-PEG was approximately 3.2 times more effective than tobramycin. Specifically, Tob-PEG had minimum inhibitory concentrations (MIC80) concentrations of 27.8 μmol/L compared to 89.8 μmol/L for tobramycin in *P. aeruginosa* pre-formed biofilm. These effects were supported by microscopy imaging of *P. aeruginosa* pre-formed biofilm that showed significant differences between the treatment groups and the absence of extracellular matrix material following treatment with Tob-PEG, in contrast to tobramycin. The time dependent antibacterial effects of Tob-PEG were not diminished as compared to tobramycin and, despite a lower MIC80, the effects on *P. aeruginosa* in pre-formed biofilm phase was observed for 18 h. A pegylated aminoglycoside such as, e.g., Tob-PEG, may be used in some embodiments to more effectively kill and/or overcome resistance of bacteria due to biofilm formation.

II. Pegylation of Aminoglycosides

In various aspects, an aminoglycoside may be pegylated and used to treat a bacterial infection such as a biofilm infection. As described herein, various methods may be used for pegylating an aminoglycoside. In some embodiments, another water-soluble polymer may be substituted for the poly(ethylene glycol) such as, e.g., poly(alkylene glycol), poly(oxyethylated polyol), poly(olefinic alcohol), poly(vinylpyrolidone), poly(hydroxypropylmethacrylamide), poly (α-hydroxy acid), poly(vinyl alcohol), polyphosphazene, polyoxazoline, and copolymers and terpolymers thereof. Other suitable polymers include heparosan and heparans, heparin, hyaluronans, N-acetylheparosan, poly[sialic acid] (PSA) and hydroxyethyl modified starch (HES).

"PEG", "polyethylene glycol", and "poly(ethylene glycol)" are used interchangeably herein to refer to a compound comprising the repeating unit $-[O-CH_2-CH_2]_n-$. For example, the PEG may comprise the structure $CH_3-[O-CH_2-CH_2]_n-$ (mPEG) or $H-[O-CH_2-CH_2]_n-$. Polyethylene glycol is an example of a PEG and refers to a compound with the structure $H-[O-CH_2-CH_2]_n-OH$. As would be recognized by one of skill in the art, a wide variety of sizes of PEG may be used to pegylate an aminoglycoside such as tobramycin. For example, in some embodiments, n=2-4000, 2-3000, 2-2000, 50-4000, 50-3000, 50-2000, 100-2000, 100-750, or 250-1000. In some embodiments, the PEG has a molecular weight of 100-10000, 2000-20000, or 2000-10000 daltons. In some embodiments, the PEG has a molecular weight of 1500-7500, 4000-6000, or about 5000 daltons. In some embodiments, the PEG is PEG 5 k. In some embodiments, the PEG has the formula $CH_3—PEG-OC(O)CH_2CH_2C(O)OH$ or $CH_3—[O—CH_2—CH_2]_n—OC(O)CH_2CH_2C(O)OH$. Generally, attaching or coupling PEG to a compound may increase the water-solubility of the compound (Greenwald, et al., 1995).

Although PEG may used to pegylate an aminoglycoside in various embodiments, in some embodiments, a modified PEG may be covalently bonded to an aminoglycoside. Modified PEG moieties are known and may comprise the formula $H—[O—CH_2—CH_2]_n—$. The n in the formula of the modified PEG have a range as defined above. The modified PEG may have the structure $H—[O—CH_2—CH_2]_n$ —(leaving group), wherein the leaving group is defined below. For example, the leaving group may be, e.g., —OH (e.g., as present in —OC(O)CH_2CH_2C(O)OH or other esters), —OMs, —OTf, —OMe, or —OTs. After pegylation, the PEG moiety may be covalently bound to the aminoglycoside moiety via an amide, etc. bond.

A "leaving group" when used as described above is a functional group which converts the hydroxyl group into a better leaving group. This functional group makes the hydroxyl group a better leaving group by stabilizing the charge on the oxygen when the atom bears a negative charge. This functional group makes the hydroxyl group more susceptible to a nucleophilic attack and displacement by nucleophilic groups.

A variety of aminoglycosides may be pegylated in various aspects of the present invention. In some embodiments, the aminoglycoside is tobramycin. Tobramycin has the structure:

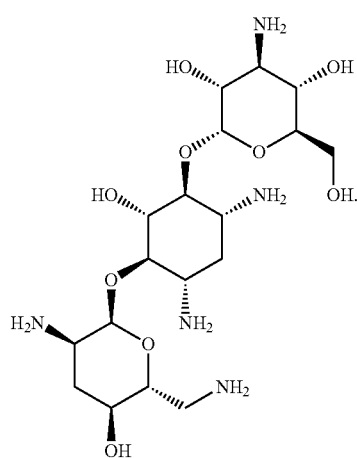 [SMILES: NC[C@H]1O[C@H](O[C@H]2[C@H](O)[C@@H](O[C@H]3O[C@H](CO)[C@@H](O)[C@H](N)[C@H]3O)[C@H](N)C[C@@H]2N)[C@H](N)C[C@@H]1O]

Tobramycin, an aminoglycoside antibiotic, is a broad-spectrum antibiotic used to treat Gram-negative infections, including *Pseudomonas* (Mesaros et al., 2007; de Hoog et al., 2007). Its mechanism of action involves interfering with protein synthesis by binding RNA, which results in the death of bacteria. In the clinic, TOBI (Tobramycin Inhalation Solution, USP) was developed to treat cystic fibrosis patients with Pseudomonal infections (Tre-Hardy et al., 2009; Woodward et al., 2010). In various embodiments, the aminoglycoside may be, e.g., gentamicin, amikacin, streptomycin, neomycin, paromomycin, netilmicin, tobramycin, kanamycin, paramecin, azithromycin, including pharmaceutically acceptable salts and esters thereof. In addition to aminoglycosides, antibacterial drugs that may be pegylated, covalently attached to a water soluble polymer as described above, or administered in combination with a pegylated aminoglycoside include, but are not limited to, rifamycins such as rifampicin, nitrofurantoin, triclosan, trimethoprim; nalidixic acid; glycopeptide antibiotics such as vancomycin; beta lactams such as cefotaxime; tetracyclines such as doxycycline, minocycline, and tetracycline; fluoroquinolone drugs such as ciprofloxacin, levofloxacin, trovafloxacin, and gemifloxacin. Antifungal drugs that may be pegylated in various embodiments of the present invention or administered in combination with a pegylated aminoglycoside include, but are not limited to, gentian violet, flucytosine, and azole drugs, such as fluconazole, miconazole, itraconazole, ketoconazole, and clotrimazole. Polyene antifungals that may be pegylated or administered in combination with a pegylated aminoglycoside include Amphotericin B, Candicidin, Filipin, Hamycin, Natamycin, Nystatin and Rimocidin, and Imidazole, triazole, and/or thiazole antifungals may be used. Echinocandins antifungals such as Anidulafungin, Caspofungin, and/or Micafungin may be used as well. Chlorhexidine may also be pegylated or included in a composition comprising a PEGylated aminoglycoside. Combinations of the foregoing antimicrobial agents may also be used together in an antimicrobial barrier or composition of the present invention; for example, the "Gendine" combination of gentian violet and chlorhexidine. Other combinations include, but are not limited to minocycline with fluconazole, gentian violet with ciprofloxacin, triclosan with fluconazole, and trimethoprim with levofloxacin.

Modifying existing drugs as polymer conjugates may be performed via different methods (e.g., Veronese et al., 2005; Lopina, 2003; Alconcel et al., 2011). Some evidence has been provided that biofilm matrix components may bind antibiotics (Stewart, 1996; Costerton et al., 1999). Without wishing to be bound by any theory, the results provided herein support the idea that pegylation of an antimicrobial, such as an aminoglycoside such as, e.g., tobramycin, may facilitate penetration of the compound into the biofilm and improve efficacy of killing of bacteria in biofilms.

Various methods may be used to attach a PEG to an aminoglycoside. For example, the terminus of a PEG may be activated to include a functional group or leaving group at the terminus. Generally, the functional group or leaving group can react with certain moieties on compound, such as an amino group, thus forming a PEG-compound conjugate. Many activated derivatives of PEG have been described. An example of such an activated derivative is the succinimidyl succinate "active ester": $CH_3O-PEG-O_2C—CH_2CH_2—CO_2—NS$. The succinimidyl succinate "active ester" may be generated, e.g., by reacting $CH_3O-PEG-O_2C—CH_2CH_2—COOH$ with NHS. In some embodiments, the succinimidyl succinate "active ester" is commercially available. In some embodiments, the below synthesis (Scheme 1) is used to pegylate tobramycin.

Typically small molecular weight drugs require the release of the polymer conjugate prior to action so that the drug is released to exploit its activity. However, as seen with PEG conjugated to tobramycin in the examples below, this is not a requirement. It would be understood that methods that have been developed to release the drugs from the conjugate in controlled conditions could be used. For example, drug release may be performed using special linkers or bonds between the polymer and the drug. These might be hydrolyzed by the acidic pHs of such as found in biofilms and cellular endosome (e.g., N-cisaconityl acid spacer and hydrazon linkages) or by enzymes (e.g., linkers such as H-Gly-Phe-Leu-Gly-OH or H-GlyLeu-Phe-Gly-OH spacers).

Scheme 1:

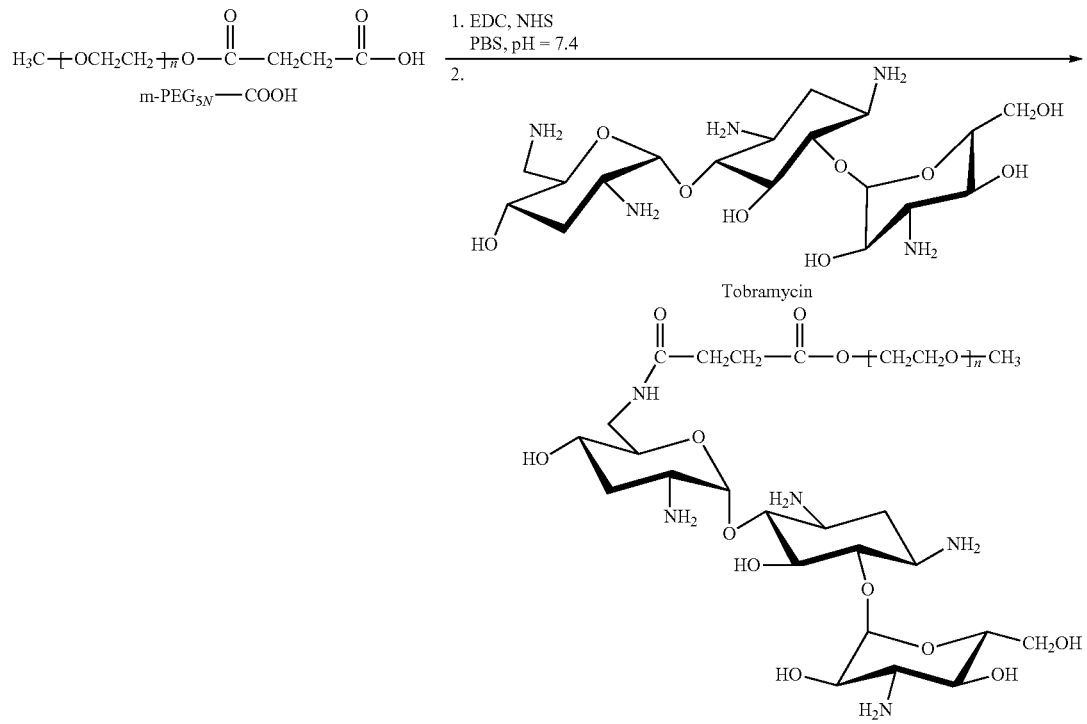

Schematic Illustration of an Example Poly(Ethylene Glycol) Modified Tobramycin

III. Pharmaceutical Preparations

Pharmaceutical compositions of the present invention may comprise an effective amount of one or more pegylated aminoglycoside (e.g., pegylated tobramycin) or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one pegylated aminoglycoside or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The pegylated aminoglycoside may be combined with different types of carriers depending on whether it is to be administered in solid, liquid or aerosol form, and whether it need to be sterile for such routes of administration as injection. A pegylated aminoglycoside (e.g., a pegylated tobramycin) of the present invention may be administered intravenously, intradermally, transdermally, intrathecally, intraarterially, intraperitoneally, intranasally, intravaginally, intrarectally, topically, intramuscularly, subcutaneously, mucosally, orally, topically, locally, via inhalation (e.g., aerosol inhalation), injection, infusion, continuous infusion, spray, localized perfusion bathing target cells directly, via a catheter, via a lavage, in cremes, in lipid compositions (e.g., liposomes), or by other method or any combination of the forgoing as would be known to one of ordinary skill in the art (see, for example, Remington: The Science and Practice of Pharmacy, 21$^{st}$ Ed. Lippincott Williams and Wilkins, 2005).

The pegylated aminoglycoside of the present invention may be formulated into a composition in a free base, neutral or salt form. Pharmaceutically acceptable salts, include the acid addition salts, e.g., those formed with the free amino groups, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations may be easily administered in a variety of dosage forms such as formulated for parenteral administrations such as injectable solutions, or aerosols for delivery to the lungs, or formulated for alimentary administrations such as drug release capsules and the like.

Further in accordance with the present invention, the pegylated antimicrobial, such as an aminoglycoside may be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the pegylated aminoglycoside may be combined with the carrier in any convenient and practical manner, e.g., by solution, suspension, emulsification, admixture, encapsulation, absorption and the like. Such procedures are routine for those skilled in the art.

In a specific embodiment of the present invention, the pegylated aminoglycoside may be combined or mixed thoroughly with a semi-solid or solid carrier. The mixing can be carried out in any convenient manner such as grinding. Stabilizing agents can be also added in the mixing process in order to protect the composition from loss of therapeutic activity, e.g., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle composition that include a pegylated aminoglycoside of the present invention, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the pegylated aminoglycoside of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. When a pharmaceutical composition comprising a pegylated aminoglycoside (e.g., pegylated tobramycin) is administered topically, the dose may be about 1.5-10 fold less, or about 2-50 times less than the dose, on a molar basis, of tobramycin or other antimicrobial. Additional examples of formulations that may be employed with the present invention include, e.g., those described in WO 1998043650 A1, U.S. Pat. No. 8,168,598, and EP 2662093, which are incorporated by reference herein in their entirety.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Microorganism Culturing

*Pseudomonas aeruginosa* (*P. aeruginosa*) PAO1 was used throughout the study. Blood agar and Brain heart infusion (BHI) solution were used for culturing *P. aeruginosa*.

Prior to each experiment, *P. aeruginosa* was cultured on blood agar for 18 h at 37° C. A loopful of the overnight bacterial growth was inoculated into BHI medium, and incubated for 18 h in an orbital shaker (80 rpm) at 37° C. The resultant growth was harvested, washed twice in Phosphate Buffered Saline (PBS, pH 7.4) and resuspended. The concentration of *P. aeruginosa* was adjusted to $1 \times 10^7$ cells/mL by spectrophotometry and confirmed by hemocytometric counting.

Biofilm Formation

*P. aeruginosa* biofilm was developed as described (Bandara et al., 2010) with minor modifications. Commercially available pre-sterilized, polystyrene, flat bottom 96-well microtiter plates (BD Biosciences, California, USA) were used. At first, 100 μL of a standard cell suspension of bacteria ($10^7$ cells/mL) was transferred into the wells of the microtiter plate, which was incubated for 1.5 h (37° C., 75 rpm) to promote microbial adherence to bottom surface of the wells. After the initial adhesion phase, the cell suspension in wells was aspirated and each well was washed twice with PBS to remove loosely adherent cells. Then, 200 μl of BHI was added into plate, followed by reincubated for 24 h (37° C., 75 rpm). Prior to the evaluation of drug delivery systems on this pre-formed biofilm, wells were washed twice with PBS to eliminate traces of the medium.

Synthesis of Tob-PEG

Tob-PEG was prepared as shown in Scheme 1, through a modified method (Wu, et al., 2008; Luten et al., 2008; Popielarski et al., 2005). In brief, 1-Ethyl-3-(3-dimethylaminopropyl)carbodiimide hydrochloride (EDC•HCl, AnaSpec Inc., Fremont, Calif., 1 mmol) and N-Hydroxysuccinimide (NHS, Aldrich, St. Louis, Mo., 1 mmol) were added into a 50 mL triangle flask containing 15 mL PBS buffer of PEG-COOH. After the above mixture was stirred at room temperature overnight, tobramycin sulfate (1 mmol) was added, then continuing for another overnight reaction. The resulting product was dialysis against distilled water, and dried through lyophilization (Scheme 1). Nuclear magnetic resonance (NMR) spectra of the final product of Tob-PEG were recorded (Varian DirectDrive 400 spectrometers) at 400 MHz Determination of Minimum Inhibitory Concentration ($MIC_{80}$) in Planktonic Phase Briefly, bacterial cell suspension ($5 \times 10^5$ cells/mL) were treated with the antibiotic in a concentration gradient and incubated in a 96 well microtiter plate for 24 h at 35° C. At the end of the incubation, the optical density of the bacterial growth was measured by a spectrophotometer at 595 nm. The lowest concentration of the antibiotic at which 80% of bacterial growth inhibition was achieved was considered as the $MIC_{80}$ of this antibiotic against *P. aeruginosa*. The assay was performed quadruplicates at three times.

Determination of Minimum Inhibitory Concentration ($MIC_{80}$) in Biofilm Formation Phase Bacterial cell suspension was added in sterile 96 well plates and incubated for 90 min under similar conditions as described in the section of Biofilm Formation. After the initial adhesion phase, adherent cells were treated with different samples in a concentration gradient, including control (PBS), tobramycin, and Tob-PEG. After 24 h incubation under 37° C. and 80 rpm, reduction assay of 2,3-bis (2-methoxy-4-nitro-5-sulfo-phenyl)-2H-tetrazolium-5-carboxanilide (XTT) was performed to quantify the viability of biofilm and crystal violet assay was used to measure biofilm biomass.

Determination of Minimum Inhibitory Concentration ($MIC_{80}$) in Pre-Formed Biofilm Phase

*P. aeruginosa* pre-formed biofilm was developed after 24 h incubation of adherent cells in sterile 96 well plates, as described in the section of Biofilm Formation. Pre-formed Biofilm were washed twice with PBS and different samples in BHI, including control (PBS), tobramycin, PEG, physical mixture of PEG and tobramycin, and Tob-PEG, were added in a concentration gradient. The plates were then incubated for 24 h at 37° C. and 80 rpm. At the end of incubation period, XTT reduction assay was performed to quantify the viability of biofilm and crystal violet assay was used to measure biofilm biomass.

Elimination of Pre-Formed Biofilm in Time Dependent Test

*P. aeruginosa* pre-formed biofilm was developed as described previously and was treated with different samples at respective biofilm $MIC_{80}$ concentrations. The plates were then incubated for 24 h at 37° C. and 80 rpm. XTT reduction assay was performed to selected samples at predetermined time points (1 h, 2 h, 3 h, 4 h, 5 h, 6 h, 9 h, 12 h, 15 h, 18 h, 21 h, 24 h and 36 h after incubation) to assess the percentage of time dependent bacterial inhibition.

Crystal Violet Assay

At the end of incubation of both test and control biofilm, crystal violet assay was performed to quantify biofilm biomass. Biofilm was carefully washed twice with PBS and stained with 1% crystal violet solution for 15 min at 25° C. without shaking. Wells were carefully washed three times with PBS to remove excess stain and air dried in room temperature. Thirty percent acetic acid was added to the wells containing stained biofilm and incubated for 20 min at 25° C. The solution was transferred to a new well plate and optical density was measured at 570 nm.

Confocal Laser Scanning Microscopy

*P. aeruginosa* pre-formed biofilm was developed as described previously and was treated with different samples at $MIC_{80}$ concentrations. The plates were then incubated for 24 h at 37° C. and 80 rpm. In the end of incubation, pre-formed biofilm in plate was stained with Live and Dead stain (Live/Dead BacLight Bacterial Viability kit, Invitrogen, Eugene, Oreg., USA). The biofilm was then analyzed by confocal laser scanning microscopy (Leica TCS SP5, Leica Microsystems, IL, USA).

Scanning Electron Microscopy

Pre-formed biofilm on glass cover slips was developed and was treated with different samples as described above. After incubation, slips were removed from the wells, washed twice with PBS and fixed with aldehyde mixture for 3 h in ice bath followed by reduced osmium tetroxide in a microwave (2 min on, 2 min off, 2 cycles, Pleco Biowave, 100 w). Slips were then washed in distilled water, dehydrated in a series of ethanol washes (50%, 70%, 95%, and 100% for 10 min), and dried in a critical point dryer (>40° C., >1200 psi, Samdri-790 Critical point Dryer, Tousimis Research Co., Maryland, USA) prior to sputter coating with Platinum/Palladium (Cressington sputter coater 208 HR). The surface topographies of the biofilm on slips were visualized with a scanning electron microscope (Zeiss Supra 40VP) in high-vacuum mode at 5 kV.

Example 2

Polyethylene Glycol Conjugated Tobramycin has Greater Antimicrobial Activity Compared to Tobramycin in *P. aeruginosa* Biofilms Synthesis of Tob-PEG Following synthesis, we utilized nuclear magnetic resonance (NMR) spectroscopy to obtain the H-NMR spectrum (FIG. 1) (Szilagyi, 1987) and help confirm the identity of Tob-PEG. In FIG. 1-A, the multiplet at around 5.45 ppm could be assigned to the H at A1', while multiplet of 4.9 ppm corresponds to the H at C1"; the two H at A3' had two correlations with the signals at about 2.1 ppm and 1.75 ppm; and the two H at B2 were linked with the peaks at about 2.05 ppm and 1.45 ppm. Compared with H-NMR spectrum of tobramycin, the peaks from 1.4 ppm to 2.1 ppm were slightly shifted to left in the H-NMR spectrum of Tob-PEG, but overall, the NMR spectrum kept a similar pattern as seen with tobramycin. In the Tob-PEG it could be observed that the characteristic three peaks signals of tobramycin were retained and no similar peaks were observed in PEG spectrum. The reason of the slight shift might be due to the interference of PEG. The peaks at 5.50 ppm and 4.95 ppm in the H-NMR spectrum of Tob-PEG matched well with that of Tobramycin as described above, while these characterized peaks were absence in the H-NMR spectrum of PEG. Within the range of around 3 ppm to 4 ppm, multiplets overlapped with each other. It could be concluded that tobramycin was successfully linked with PEG through chemical reaction.

Antimicrobial Testing

Tobramycin had lower MIC in *P. aeruginosa* planktonic phase and biofilm formation The broth microdilution assay revealed that the $MIC_{80}$ for tobramycin was 1.4 μmol/L whereas it was 13.9 μmol/L for Tob-PEG (FIG. 2) *P. aeruginosa* planktonic phase. Similar results were achieved in *P. aeruginosa* biofilm formation phase. According to XTT reduction assay, the critical concentration of tobramycin necessary for 80% suppression of *P. aeruginosa* viability was 1.4 μmol/L and it was 13.9 μmol/L for Tob-PEG.

Tob-PEG possessed superior activity in eliminating of *P. aeruginosa* pre-formed biofilm.

Figure 3:
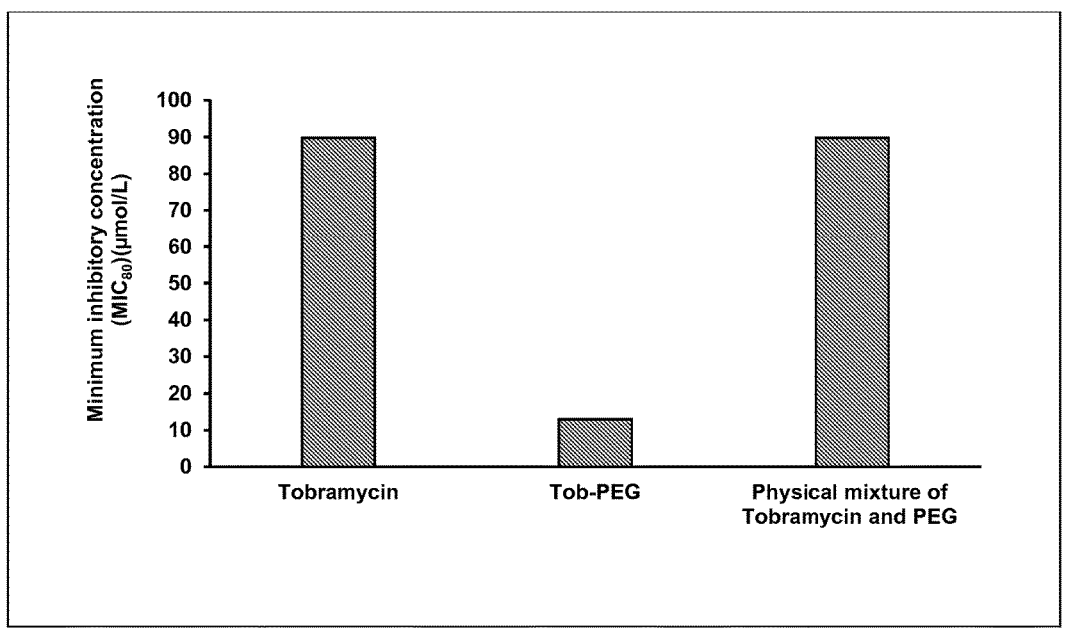
FIG. 3: Minimum inhibitory concentration (MIC80) of tobramycin, Tob-PEG, and physical mixture of tobramycin and PEG in *P. aeruginosa* pre-formed biofilm. (MIC80±SD, SD=0, n=12, experiments were performed in quadruplicates at three times. The broth dilution assay resulted in the same value of the drug concentration for MIC80, thus SD is 0); note that the Tob-PEG exhibited significant lower MIC80 compared to physical mixed tobramycin and PEG.

XTT reduction assay data revealed that the critical concentration of tobramycin needed for 80% inhibition of viable *P. aeruginosa* pre-formed biofilm was 89.80 μmol/L and it was 27.81 μmol/L for Tob-PEG. Physically mixed tobramycin and PEG also showed similar concentration as pure tobramycin (89.80 μmol/L) in eliminating established *P. aeruginosa* biofilm (FIG. 3).

Quantification of Biofilm Biomass

Figure 4:
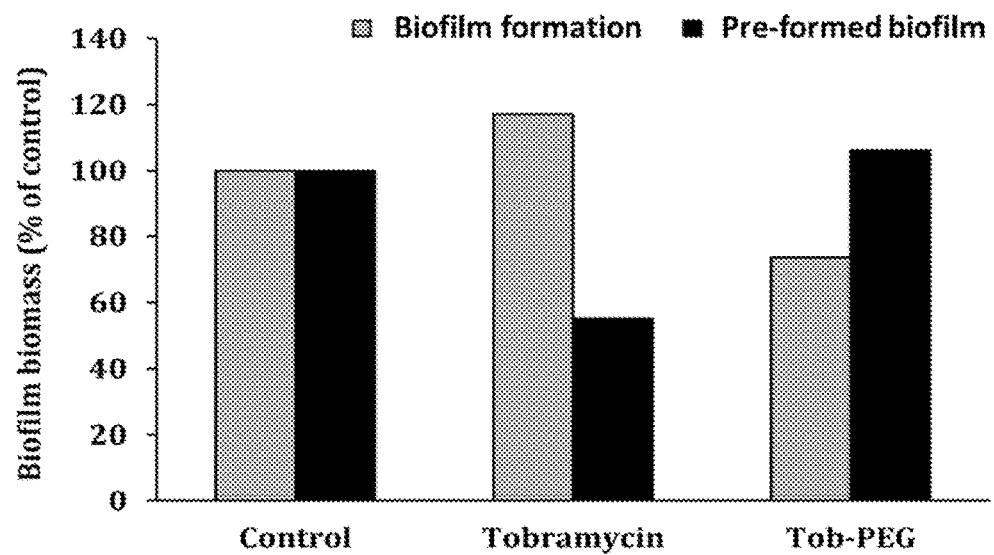
FIG. 4: Inhibition of biofilm biomass of *P. aeruginosa* after antibiotic treatment.

Biofilm biomass was measured by crystal violet assay. In the biofilm formation phase, after treatment of 1.40 μmol/L tobramycin, 17% increment of the biofilm biomass was observed compared to control, while Tob-PEG resulted in 26% less after 24 h. In the pre-formed biofilm, the biomass of Tob-PEG (27.81 μmol/L, $MIC_{80}$) treated biofilm was as same as the untreated controls. Whereas, the biomass of tobramycin (27.81 μmol/L, $MIC_{80}$) treated biofilm was only 55% of the control biofilm and 52% of the Tob-PEG treated samples (FIG. 4).

Time Dependent Biofilm Inhibition by Tob-PEG

Figure 5:
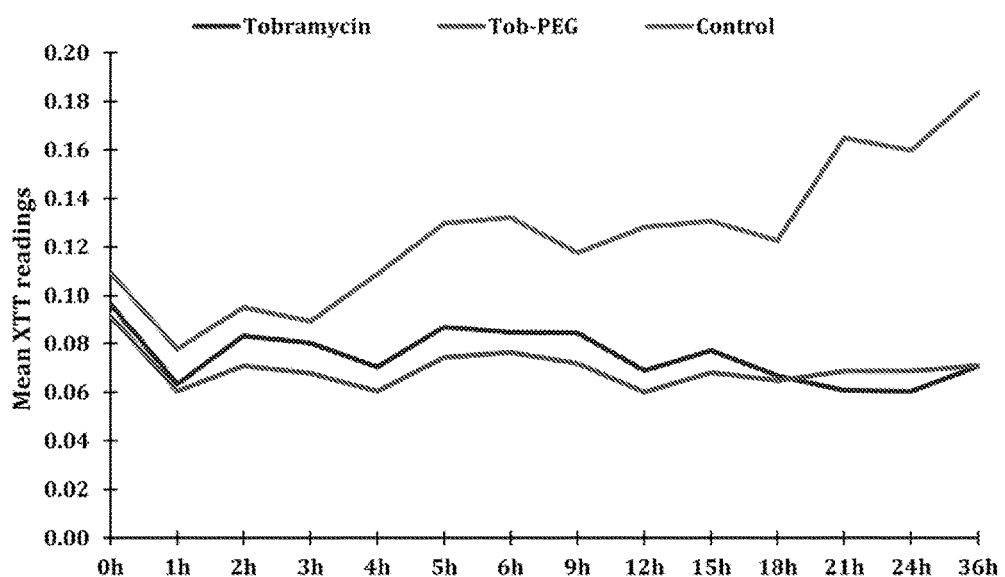
FIG. 5: Time dependent survival of *P. aeruginosa* in pre-formed biofilm treated with antibiotics.

Tob-PEG with its $MIC_{80}$ concentration (27.81 μmol/L) exhibited the stronger inhibition effect upto 18 h than pure tobramycin treatment with MIC80 concention of 89.80 μmol/L. After 18 h, tobramycin was superior compare to Tob-PEG. However, both treatment of Tob-PEG and tobramycin showed similar reduction toward *P. aeruginosa* pre-formed biofilm (FIG. 5).

Confocal Laser Scanning Microscopy

Control *P. aeruginosa* pre-formed biofilm was densely colonized, well-structured and consisted of abundant extracellular substances. Higher proportion of bacterial cells in the biofilm appeared to be live (FIG. 6A). After incubation with pure PEG, pre-formed biofilm showed similar structure as controlled group; bacterial cells were embedded in a considerable mass of extracellular matrix (FIG. 6B). In contrast, pure tobramycin treated biofilm was scanty and high proportion of dead cells were visible. Moreover, Tob-PEG treated biofilm showed isolated colonies of dead bacteria cells (FIG. 6D).

Scan Electron Microscopy

Figure 7A:
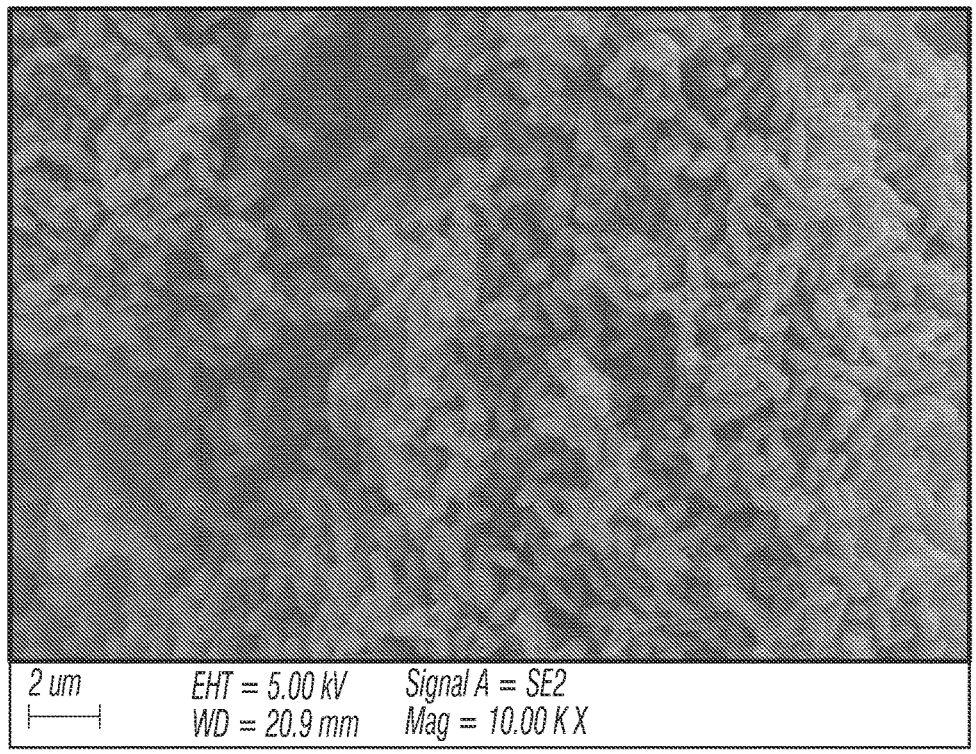
FIGS. 7A-D: SEM images of *P. aeruginosa* biofilm (×10000).
Figure 7B:
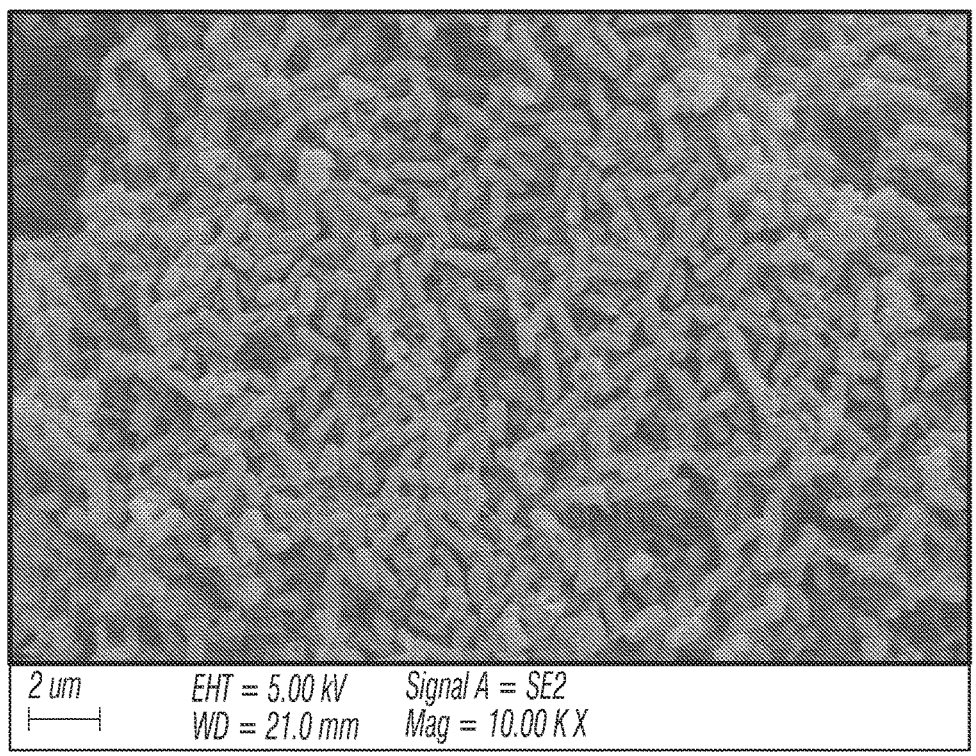
Figure 7C:
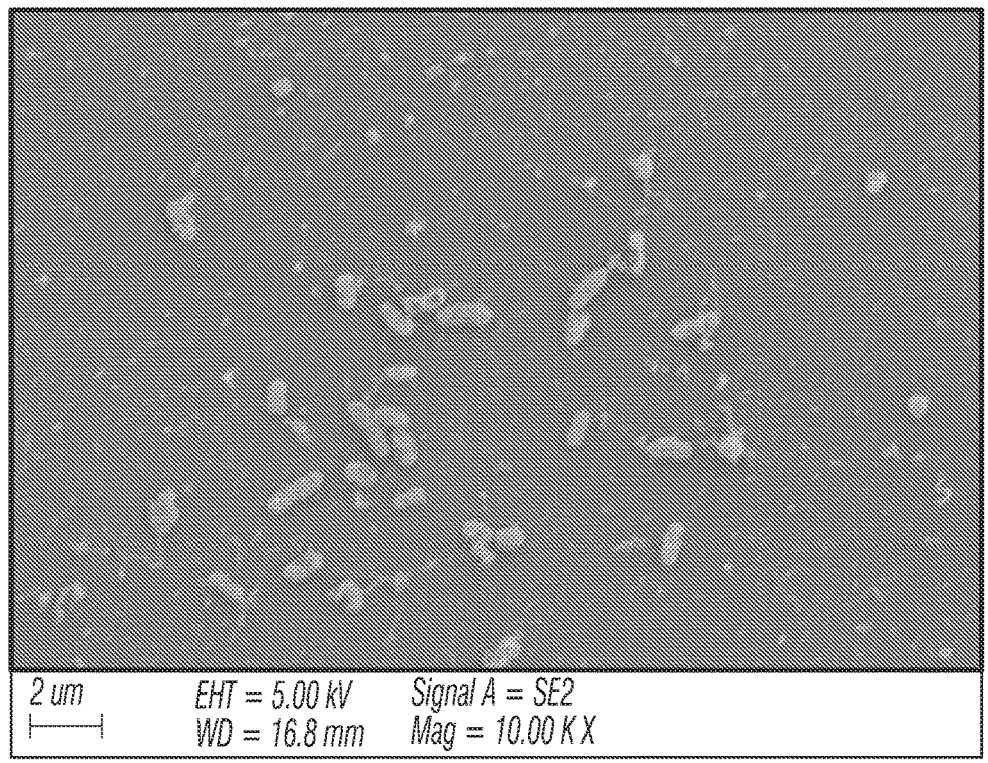
Figure 7D:
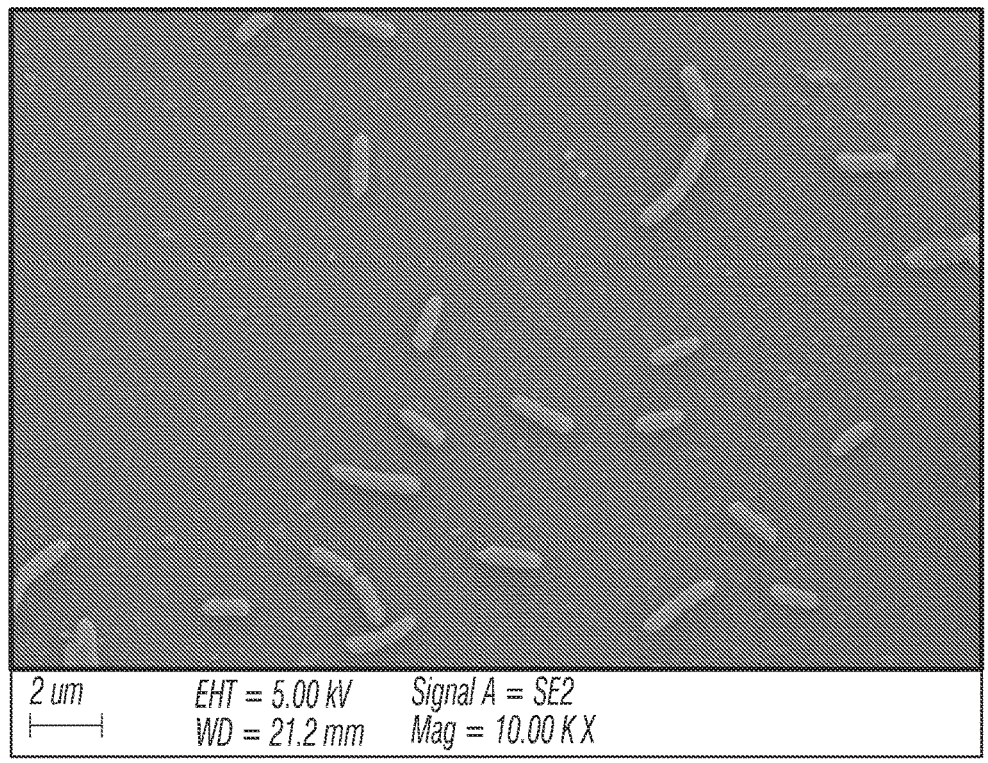

Control *P. aeruginosa* pre-formed biofilm showed a densely colonized, well defined and spatially oriented biofilm, in which extracellular matrix was clearly visible (FIG. 7A). Similarly, PEG treated biofilm was also dense and well organized with extracellular matrix (FIG. 7B). Both tobramycin and Tob-PEG treated biofilm showed greatly disrupted biofilm and few scattered bacterial cells (FIGS. 7C-D). However, some extracellular matrix was still present in pure tobramycin treated biofilm compared to Tob-PEG treated biofilm (FIGS. 7C-D).

Anti-Microbial Testing in *P. aeruginosa* Planktonic Phase

In planktonic phase of *P. aeruginosa*, the $MIC_{80}$ for free tobramycin was significantly lower (1.40 μmol/L) than that of the Tob-PEG (13.90 μmol/L), which represents an approximate 10 fold reduction in activity of Tob-PEG against planktonic *P. aeruginosa*. Several reasons for the apparent lower antimicrobial activity of TOB-PEG can be proposed. However, some background on the mechanism of action and structure of tobramycin should be considered. Tobramycin is an aminoglycoside antibiotic. Aminoglycosides are hydrophilic sugars with amino and hydroxyl functionalities (Kotra et al., 2000). The amine moieties become protonated in physiological conditions making the drug polycationic. Due to this polycationic nature, aminoglycosides like tobramycin show binding affinity for nucleic acids. Specifically, aminoglycosides possess high affinities for certain portions of RNAs, especially the prokaryotic 16S rRNA (Kotra et al., 2000). This bacterial small ribosomal subunit has been identified as the primary target of aminoglycosides and inhibits the translation process by causing misreading and/or hindering the translocation step (Magnet and Blanchard, 2005). They also they show binding affinity for negatively charged residues in the outer membrane of Gram-negative bacilli (Jana and Deb 2006).

Thus, in interpreting the anti-microbial activity in the planktonic phase experiments, the conjugation of PEG to the tobramycin molecule could diminish the binding efficiency to the 16S rRNA due to steric hindrance (the PEG molecular weight has an average of 5000 Da) compared to non-conjugated tobramycin. In addition, the conjugation of the PEG to the 6' amine group of tobramycin would yield a molecule with decreased the cationic nature. Furthermore, the cellular uptake process of tobramycin into the bacteria had been reported to be self-promoted involving the amino-glycoside-induced disruption of $Mg^{2+}$ bridges between adjacent lipopolysaccharide molecules in the outer membrane (Jana and Deb, 2006; Hancock et al., 1991). Thus, PEG conjugation might also decrease significantly this uptake mechanism and consequently affect its cellular uptake efficiencies. These different mechanisms would be explored in future studies with Tob-PEG. In these studies it was important to note that PEG alone, as a control, did not suppress P. aeruginosa growth in planktonic phase, thus indicating that PEG was not an inhibitor or promoter of microbial activity (FIG. 3).

Anti-Microbial Testing in P. aeruginosa Biofilm Formation Phase

Similar to planktonic phase results, the Tob-PEG showed less activity than tobramycin during P. aeruginosa biofilm formation (FIG. 2). In fact, the 80% inhibition concentrations for Tob-PEG (13.90 µmol/L) was identical to that observed in the planktonic phase experiments (FIG. 2). This is consistent with our hypothesis that the apparent lower activity of the Tob-PEG might be caused by steric hindrance and decreased binding affinities as described previously.

In contrast, however, the biomass measured by the crystal violet assay showed improved activity of Tob-PEG with respect to biofilm mass during biofilm formation phase. Tob-PEG resulted in lower biomass (−26% change versus untreated control) whereas tobramycin treated samples resulted in higher biomass development (+17% change versus control) in the biofilm formation phase. These observations of increased biofilm mass with treatment of tobramycin were consistent with previous reports and may be explained by the protective response of the bacterial to the treatment with aminoglycosides (Hoffman et al., 2005). Hoffman et al. demonstrated that biofilm formation could be a specific, defensive reaction to the presence of antibiotics specifically in the case of tobramycin in P. aeruginosa (Hoffman et al., 2005). The decrease in biofilm mass during biofilm formation phage upon treatment with Tob-PEG was more difficult to explain, but might be related to the lower intrinsic activity of the Tob-PEG molecule. In addition, in P. aeruginosa, the aminoglycoside response regulator (arr) gene, which was found essential for the tobramycin-induction of biofilm formation, may not be influenced by the Tob-PEG molecule as it is by free tobramycin.

Anti-Microbial Testing in P. aeruginosa Pre-Formed Biofilm Phase

Consistent with previous data, the concentration of tobramycin needed for 80% inhibition of viable P. aeruginosa in pre-formed biofilm phase was 89.80 µmol/L. However, Tob-PEG, despite its lower activity in planktonic phase, had significantly higher activity in pre-formed biofilm models, 27.81 µmol/L (FIG. 2). The physical mixture of tobramycin and PEG showed similar activity as pure tobramycin 89.80 µmol/L in eliminating pre-formed P. aeruginosa biofilm (FIG. 3). Thus, these data indicated that Tob-PEG was significantly more effective at treating mature biofilm than free tobramycin. Moreover, FIG. 5, showing the time dependent activity of both free tobramycin and Tob-PEG dosed at their respective $MIC_{80}$ concentrations, indicated that the higher activity of Tob-PEG was durable.

Consistent with the antimicrobial activity and biofilm biomass study, the microscopy studies also indicated important differences between the free tobramycin and Tob-PEG treatment. In the live-dead staining using fluorescence imaging (FIGS. 6A-D), it was obvious that although both treatments were dosed at the $MIC_{80}$ concentrations, the Tob-PEG treated P. aeruginosa biofilm demonstrated a severe destruction of the biofilm structure and greater proportions of dead and dying bacterial cells compared to tobramycin treated biofilm, showing the superior antibiofilm activity of former over the latter. Although, tobramycin could disrupt P. aeruginosa pre-formed biofilm, it was evident that the biofilm structure was somewhat preserved with higher proportions of living cells and a considerable extracellular materials. Interestingly, PEG treated biofilm showed healthy three dimensional structures with proportionate live and dead cells and extracellular matrix compared to tobramycin and Tob-PEG treated pre-formed biofilm confirming that PEG itself had minimal effects on P. aeruginosa pre-formed biofilm. Despite extensive sample preparations and possibility of washing away the extracellular materials, scanning electron microscopic images also confirmed aforementioned findings. Both untreated control and PEG treated biofilm were dense, spatially oriented with substantial amount of extracellular materials, while tobramycin and Tob-PEG treated biofilm were completely disrupted and few scattered cells were visible. However, some extracellular materials appeared in tobramycin treated biofilm and bacterial cells were diminished and smaller in size, while Tob-PEG treated biofilm have no extracellular materials visible in the microscopic field and the bacteria appeared to be elongated. These findings further validated that Tob-PEG had a stronger effect on pre-formed biofilm matrix. It was interesting to note that despite the increased antimicrobial activity, the biomass of Tob-PEG treated biofilm, as measured by the relatively non-specific crystal violet assay, was as same as the untreated control, whereas the biomass of tobramycin treated biofilm was significantly lower (55% of the control) (FIG. 4).

Visual Alginate and Drug Interaction Study

A simple assay was developed to visually demonstrate the differences in interaction between the different drugs and formulations used in these performance studies. A volume of 50 µL alginate solution (0.5 g/100 mL) was applied to a glass slide. One drop of drug or control (tobramycin, PEG, unbound mixture of tobramycin with PEG, Tob-PEG) was added to the top of alginate solution on the glass slide using a micropipette. Immediately after applying the drop of drug solution, the slide was examined by light microscopy imaging at 15 times magnification on a Planapo 2.0× microscope (Leica M205 FA, Germany). All test samples were applied at a concentration of 1.4 mmol/L. An untreated alginate solution, PEG, and the physical blend of PEG and tobramycin were used as the control groups.

Figure 8A:
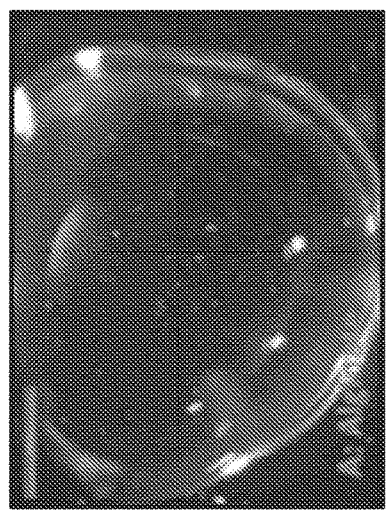
FIGS. 8A-E: Visual alginate and drug interaction study.
Figure 8B:
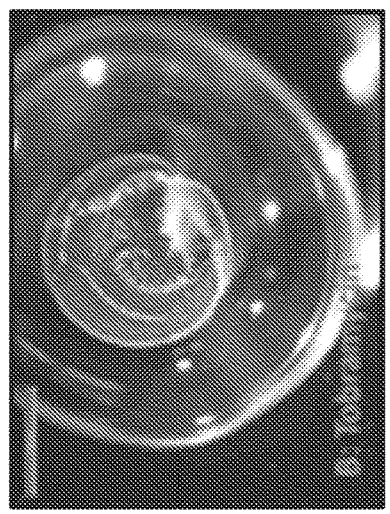
Figure 8C:
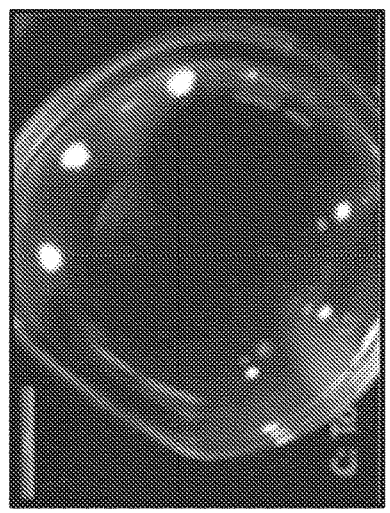
Figure 8D:
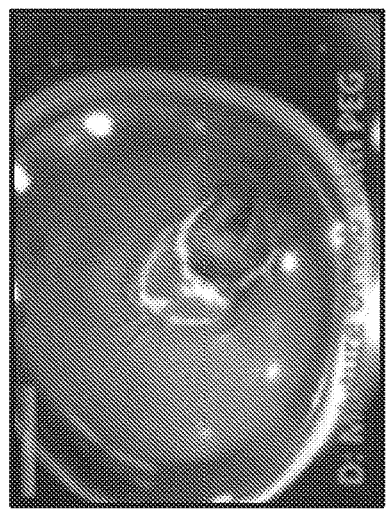
Figure 8E:
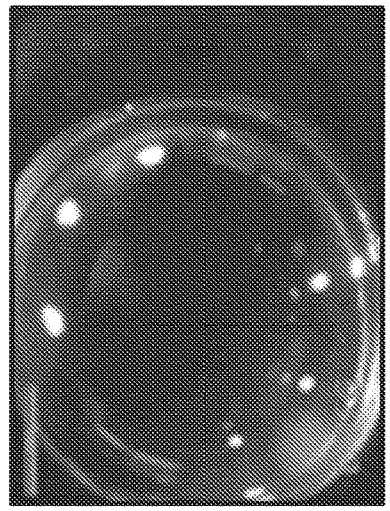

As shown in FIGS. 8A-E, the microscope image of the control, untreated alginate solution was clear and transparent. In FIG. 8B, the added drop of drug immediately produced a visible boundary between the added drug droplet and the alginate solution. This spherical formation did not dissipate with time. In FIG. 8D, the mixture of nonconjugate PEG with tobramycin resulted in a similar visible interaction between the added drop and the alginate solution, though the boundary dispersed more than with tobramycin alone. In FIG. 8C, however, the added droplet containing Tob-PEG did not result in a visible boundary. The same was observed for the added PEG solution (FIG. 8E).

Without wishing to be bound by any theory, tobramycin may bind to alginate in the bacterial biofilm through ionic interactions. These studies illustrate the clear difference in drug interactions with alginate using the PEG conjugate. As shown in FIG. 8C, no visible interaction with alginate was observed after tobramycin was chemically modified into Tob-PEG, in contrast to the unconjugated drug (FIG. 8B). The absence of interaction may be attributed to the PEG conjugated at the tobramycin 6' amine site, which reduces the overall positive charge of tobramycin. Without wishing to be bound by any theory, the inventors anticipate that the polymeric PEG, which has a molecular weight of 5000 Da, might form a hydration shield around the tobramycin, which might decrease the likelihood of physical interactions between the tobramycin and alginate. This idea is supported by the observed differences in the interactions observed in FIG. 8C and FIG. 8D. In FIG. 8D, the droplet of the added mixture of tobramycin and PEG dispersed more easily into the alginate than what was observed with tobramycin alone. This finding supports the idea that PEG, even unbound to the tobramycin, may achieve some level of shielding, though significant interactions were still observed.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 8,168,598
WO 1998043650 A1
EP 2662093
Aaron, S. D., Antibiotic synergy testing should not be routine for patients with cystic fibrosis who are infected with multiresistant bacterial organisms. Paediatr Respir Rev, 8(3): p. 256-61, 2007.
Alconcel et al., FDA-approved poly (ethylene glycol)-protein conjugate drugs. Polymer Chemistry, 2(7): p. 1442-1448, 2011.
Bandara et al., *Pseudomonas aeruginosa* inhibits in-vitro *Candida* biofilm development. BMC Microbiol, 10(1): p. 125, 2010.
Costerton et al., Bacterial biofilms: a common cause of persistent infections. Science, 284(5418): p. 1318-1322, 1999.
de Hoog et al., New dosing strategies for antibacterial agents in the neonate. Semin Fetal Neonatal Med, 10(2): p. 185-94, 2005.
Dodge et al., Cystic fibrosis mortality and survival in the UK: 1947-2003. Eur Respir J, 29(3): p. 522-6, 2007.
Flemming and Wingender, The biofilm matrix. Nature Reviews Microbiology, 8(9): p. 623-633, 2010.
Fux et al., Survival strategies of infectious biofilms. Trends Microbiol, 13(1): p. 34-40, 2005.
George et al., Cystic fibrosis infections: treatment strategies and prospects. FEMS Microbiol Lett, 300(2): p. 153-64, 2009.
Gilligan, P. H., Microbiology of airway disease in patients with cystic fibrosis. Clin Microbiol Rev, 4(1): p. 35-51, 1991.
Greenwald, et al., *J. Org. Chem.*, 60:331-336, 1995.
Hancock et al., Interaction of aminoglycosides with the outer membranes and purified lipopolysaccharide and OmpF porin of *Escherichia coli*. Antimicrobial agents and chemotherapy, 35(7): p. 1309-1314, 1991.
Hoffman et al., Aminoglycoside antibiotics induce bacterial biofilm formation. Nature, 436(7054): p. 1171-1175, 2005.
HØiby, N., Recent advances in the treatment of *Pseudomonas aeruginosa* infections in cystic fibrosis. BMC medicine, 9(1): p. 32, 2011.
Jana and Deb, Molecular understanding of aminoglycoside action and resistance. Applied microbiology and biotechnology, 70(2): p. 140-150, 2006.
Kotra et al., Aminoglycosides: perspectives on mechanisms of action and resistance and strategies to counter resistance. Antimicrobial agents and chemotherapy, 44(12): p. 3249-3256, 2000.
Luten et al., Degradable PEG-folate coated poly(DMAEA-co-BA)phosphazene-based polyplexes exhibit receptor-specific gene expression. Eur J Pharm Sci, 33(3): p. 241-51, 2008.
MacLeod et al., Aminoglycoside-resistance mechanisms for cystic fibrosis *Pseudomonas aeruginosa* isolates are unchanged by long-term, intermittent, inhaled tobramycin treatment. Journal of Infectious Diseases, 181(3): p. 1180-1184, 2000.
Magnet and Blanchard, Molecular insights into aminoglycoside action and resistance. Chemical reviews, 105(2): p. 477-498, 2005.
Mesaros et al., *Pseudomonas aeruginosa*: resistance and therapeutic options at the turn of the new millennium. Clin Microbiol Infect, 13(6): p. 560-78, 2007.
Pier, G. B., The challenges and promises of new therapies for cystic fibrosis. J Exp Med., 209(7): p. 1235-9, 2012.
Popielarski et al., A nanoparticle-based model delivery system to guide the rational design of gene delivery to the liver. 1. Synthesis and characterization. Bioconjug Chem, 16(5): p. 1063-70, 2005.
Ramsey and Wozniak, Understanding the control of *Pseudomonas aeruginosa* alginate synthesis and the prospects for management of chronic infections in cystic fibrosis. Molecular microbiology, 56(2): p. 309-322, 2005.
Ramsey et al., Intermittent administration of inhaled tobramycin in patients with cystic fibrosis. Cystic Fibrosis Inhaled Tobramycin Study Group. N Engl J Med, 340(1): p. 23-30, 1999.
Ratjen and Doring, Cystic fibrosis. Lancet, 361(9358): p. 681-9, 2003.
Ratjen, F. A., Cystic fibrosis: pathogenesis and future treatment strategies. Respir Care, 54(5): p. 595-605, 2009.
*Remington: The Science and Practice of Pharmacy*, 21$^{st}$ Ed. Lippincott Williams and Wilkins, 2005.
*Remington's Pharmaceutical Sciences*, 18th Ed. Mack Printing Company, 1990.
Shaul et al., Assessment of 6'- and 6'''-N-acylation of aminoglycosides as a strategy to overcome bacterial resistance. Org Biomol Chem, 9(11): p. 4057-63, 2011.

Stewart, P. S., Theoretical aspects of antibiotic diffusion into microbial biofilms. Antimicrobial agents and chemotherapy, 40(11): p. 2517-2522, 1996.

Strateva and Yordanov, *Pseudomonas aeruginosa*—a phenomenon of bacterial resistance. J Med Microbiol, 58(Pt 9): p. 1133-48, 2009.

Szilagyi, L., Assignments of the 1H- and 13C-n.m.r. spectra of tobramycin at low and high pH. Carbohydr Res, 170(1): p. 1-17, 1987.

Tre-Hardy et al., Evaluation of long-term co-administration of tobramycin and clarithromycin in a mature biofilm model of cystic fibrosis clinical isolates of *Pseudomonas aeruginosa*. Int J Antimicrob Agents, 34(4): p. 370-4. 2009.

Veronese et al., PEG-doxorubicin conjugates: influence of polymer structure on drug release, in vitro cytotoxicity, biodistribution, and antitumor activity. Bioconjugate chemistry, 16(4): p. 775-784, 2005.

Wagner and Iglewski, *P. aeruginosa* biofilms in CF infection. Clinical reviews in allergy & immunology, 35(3): p. 124-134, 2008.

Woodward et al., Budget impact model of tobramycin inhalation solution for treatment of *Pseudomonas aeruginosa* in cystic fibrosis patients. J Med Econ, 13(3): p. 492-9, 2010.

Wu, et al., A new biodegradable polymer: PEGylated chitosan-g-PEI possessing a hydroxyl group at the PEG end. Journal of Polymer Research, 15(3): p. 181-185, 2008.

Yang Lopina, Penicillin V-conjugated PEG-PAMAM star polymers. Journal of Biomaterials Science, Polymer Edition, 14(10): p. 1043-1056, 2003.

Zhang and Mah, Involvement of a novel efflux system in biofilm-specific resistance to antibiotics. Journal of bacteriology, 190(13): p. 4447-4452, 2008.

What is claimed is:

1. A compound comprising an aminoglycoside covalently bound to a poly(ethylene glycol), wherein the compound has the structure

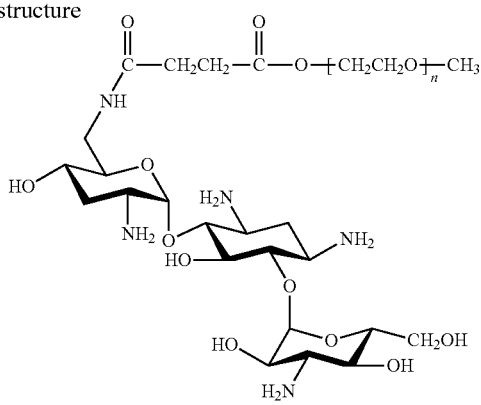

wherein n=2-3000.

2. The compound of claim 1, wherein n=100-2000.

3. The compound of claim 2, wherein n=100-750.

4. The compound of claim 2, wherein n=250-1000.

5. The compound of claim 1, wherein the compound has a molecular weight ranging from about 100 daltons to about 100,000 daltons.

6. The compound of claim 5, wherein the compound has a molecular weight ranging from about 2000 daltons to about 10,000 daltons.

7. The compound of claim 1, wherein the compound is comprised in a pharmaceutical composition.

8. The compound of claim 7, wherein the pharmaceutical composition is formulated for topical, inhalational, parenteral, intravenous, or injection administration.

9. The compound of claim 7, wherein the pharmaceutical composition comprises a second antimicrobial, antibacterial, or antifungal compound.

10. The compound of claim 9, wherein the second compound is an aminoglycoside.

11. The compound of claim 10, wherein the second compound is tobramycin.

12. A medical device, wherein at least a portion of a surface of the device is coated with the compound of claim 1.

13. The medical device of claim 12, wherein all of the surface is coated with the compound.

14. The medical device of claim 12, wherein the medical device is a glove, a catheter, a stent, a staple, a pin, an electrical nerve stimulation device, a screw, a rod, a wire, a collar, a tube, or a surgical drain.

15. The medical device of claim 14, wherein the medical device is a catheter.

16. The medical device of claim 15, wherein the catheter is an intravenous catheter, a drainage catheter, or a urinary catheter.

17. The medical device of claim 12, wherein the medical device wherein the coating further comprises a second antimicrobial, antibacterial, or antifungal compound.

18. The medical device of claim 17, wherein the second compound is an aminoglycoside.

19. The medical device of claim 18, wherein the second compound is tobramycin.

20. A method of treating a biofilm infection in a subject comprising administering to the subject a therapeutic amount of a pegylated aminoglycoside compound of claim 1.

* * * * *